(12) United States Patent
Bender et al.

(10) Patent No.: US 11,040,168 B2
(45) Date of Patent: Jun. 22, 2021

(54) COGNITIVE STRESS MANAGEMENT BY AUGMENTED REALITY (AR) CUSTOMIZATION

(71) Applicant: International Business Machines Corporation, Armonk, NY (US)

(72) Inventors: Michael Bender, Armonk, NY (US); Stan K. Daley, Atlanta, GA (US); Michael Shute, Southbury, CT (US); Siddhartha Sood, Noida (IN); Pooja Malik, Noida (IN)

(73) Assignee: International Business Machines Corporation, Armonk, NY (US)

( * ) Notice: Subject to any disclaimer, the term of this patent is extended or adjusted under 35 U.S.C. 154(b) by 239 days.

(21) Appl. No.: 16/014,376

(22) Filed: Jun. 21, 2018

(65) Prior Publication Data

US 2019/0388647 A1    Dec. 26, 2019

(51) Int. Cl.
*A61M 21/02* (2006.01)
*A61M 21/00* (2006.01)

(52) U.S. Cl.
CPC ..... *A61M 21/02* (2013.01); *A61M 2021/0027* (2013.01); *A61M 2021/0044* (2013.01); *A61M 2205/3303* (2013.01); *A61M 2205/3584* (2013.01); *A61M 2205/52* (2013.01)

(58) Field of Classification Search
CPC .......... A61M 2205/3303; A61M 21/02; A61M 2021/0044; A61M 2021/0027; A61M 2205/52; A61M 2205/3553; A61M 2205/3584; A61B 2090/365; G06F 3/011
See application file for complete search history.

(56) References Cited

U.S. PATENT DOCUMENTS

| 5,807,114 A | 9/1998 | Hodges et al. |
| 6,425,764 B1 | 7/2002 | Lamson |
| 7,128,577 B2 | 10/2006 | Renaud |
| 2005/0216243 A1 | 9/2005 | Graham et al. |

(Continued)

FOREIGN PATENT DOCUMENTS

WO    WO 2012151607 A1    11/2012

OTHER PUBLICATIONS

Anonymous, "System and Method for Cognitive Shaping via Visual Analysis." IP.com Disclosure Number: IPCOM000244312D, Publication Date: Dec. 1, 2015.
(Continued)

*Primary Examiner* — Christine H Matthews
*Assistant Examiner* — Joshua Daryl D Lannu
(74) *Attorney, Agent, or Firm* — Brian M. Restauro, Esq.; Hye Jin Lucy Song; Heslin Rothenberg Farley & Mesiti PC

(57) ABSTRACT

Methods, computer program products, and systems are presented. The methods include, for instance: preparation of a user profile for a user whose stress response is being managed to attain a goal response. A use mode is determined according to objectives for the goal response. An Augmented Reality (AR) environment customized for the user is generated according to a use mode configuration corresponding to the use mode, and delivered to the user via a user AR device. Responses by the user to the AR environment is monitored by IoT devices, cognitively analyzed, and a determination if the goal response has been attained would be made according to the monitored user response.

25 Claims, 6 Drawing Sheets

(56) References Cited

U.S. PATENT DOCUMENTS

| | | |
|---|---|---|
| 2010/0010371 A1 | 1/2010 | Zayfert et al. |
| 2011/0213197 A1 | 9/2011 | Robertson et al. |
| 2013/0009993 A1* | 1/2013 | Horseman .............. G16H 40/63 |
| | | 345/633 |
| 2016/0049094 A1 | 2/2016 | Gupta et al. |
| 2016/0077547 A1 | 3/2016 | Aimone et al. |

OTHER PUBLICATIONS

A. Senson, "Virtual Reality Therapy: Treating the Global Mental Health Crisis." Jan. 6, 2016 [Accessed Feb. 15, 2018] https://techcrunch.com/2016/01/06/virtual-reality-therapy-treating-the-global-mental-health-crisis/.

O. Baus, "Moving from Virtual Reality Exposure-Based Therapy to Augmented Reality Exposure-Based Therapy: A Review." Frontiers in Human Neuroscience. 2014; 8:112.

A. Gaggioli, "Experiential Virtual Scenarios with Real-Time Monitoring (Interreality) for the Management of Psychological Stress: A Block Randomized Controlled Trial." J Med Internet Res. Jul. 2014; 16(7): e167.

N. Carbonaro, "A mobile biosensor to detect cardiorespiratory activity for stress tracking," 2013 7th International Conference on Pervasive Computing Technologies for Healthcare and Workshops, Venice, 2013, pp. 440-445.

A. Rizzo, "Virtual Reality as a Tool for Delivering PTSD Exposure Therapy and Stress Resilience Training." Military Behavioral Health, 1: 48-54, 2013.

T. Parsons, "Virtual Reality Exposure Therapy for Anxiety and Specific Phobias." in Encyclopedia of Information Science and Technology, Third Edition, 2015 pp. 288-295.

M. Neerincx, "Virtual reality exposure and neuro-bio feedback to help coping with traumatic events." In Proceedings of the 28th Annual European Conference on Cognitive Ergonomics (ECCE '10). ACM, New York, NY, USA, 367-369, 2010.

M. Haworth, "PhoVR: a virtual reality system to treat phobias." In Proceedings of the 11th ACM SIGGRAPH International Conference on Virtual-Reality Continuum and its Applications in Industry (VRCAI '12). ACM, New York, NY, USA, 171-174, 2012.

S. Corbett-Davies, "Interactive AR exposure therapy." In Proceedings of the 13th International Conference of the NZ Chapter of the ACM's Special Interest Group on Human-Computer Interaction (CHINZ '12). ACM, New York, NY, USA, 98-98, 2012.

P. Mell, et al. "*The NIST Definition of Cloud Computing*", NIST Special Publication 800-145, Sep. 2011, Gaithersburg, MD.

\* cited by examiner

COGNITIVE STRESS MANAGEMENT BY AUGMENTED REALITY (AR) CUSTOMIZATION

TECHNICAL FIELD

The present disclosure relates to cognitive analytics and augmented reality (AR) technology, and more particularly to methods, computer program products, and systems for customizing AR environments for targeted stress levels from users.

BACKGROUND

Conventionally, certain psychological therapy methods manipulating intensity of stress level of patients have been utilized in order to treat certain psychological disorders such as posttraumatic stress disorder (PTSD) and many types of phobias. Virtual Reality (VR) or Augmented Reality (AR) technologies are also widely used in many types of simulations in areas of training and entertainment, for individual and enterprise users.

SUMMARY

The shortcomings of the prior art are overcome, and additional advantages are provided, through the provision, in one aspect, of a method. The method for cognitively managing a stress level on a user includes, for instance: preparing, by one or more processor, a user profile corresponding to the user, where the user profile comprising baseline biometrics for the stress level on the user and conditions affecting the user in responding to one or more augmented reality (AR) environment, as delivered by a user AR device, where responses by the user to the AR environment is being monitored by one or more Internet of Things (IoT) device configured for the user; determining, by the one or more processor, a use mode for the one or more AR environment, where the use mode corresponds to a use mode configuration specifying how to generate the one or more AR environment for the user to attain purposes of the use mode; selecting, by the one or more processor, AR environment content for the one or more AR environment content based on the user profile and the use mode; determining, by the one or more processor, a goal response for the user as being presented with the one or more AR environment, based on the user profile and the use mode; generating, by the one or more processor, an AR environment of the one or more AR environment according to the use mode configuration; and sending, by the one or more processor, the generated AR environment to the user AR device for the user to experience the generated AR environment.

Additional features are realized through the techniques set forth herein. Other embodiments and aspects, including but not limited to computer program products and systems, are described in detail herein and are considered a part of the claimed invention.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

DETAILED DESCRIPTION

Figure 1:
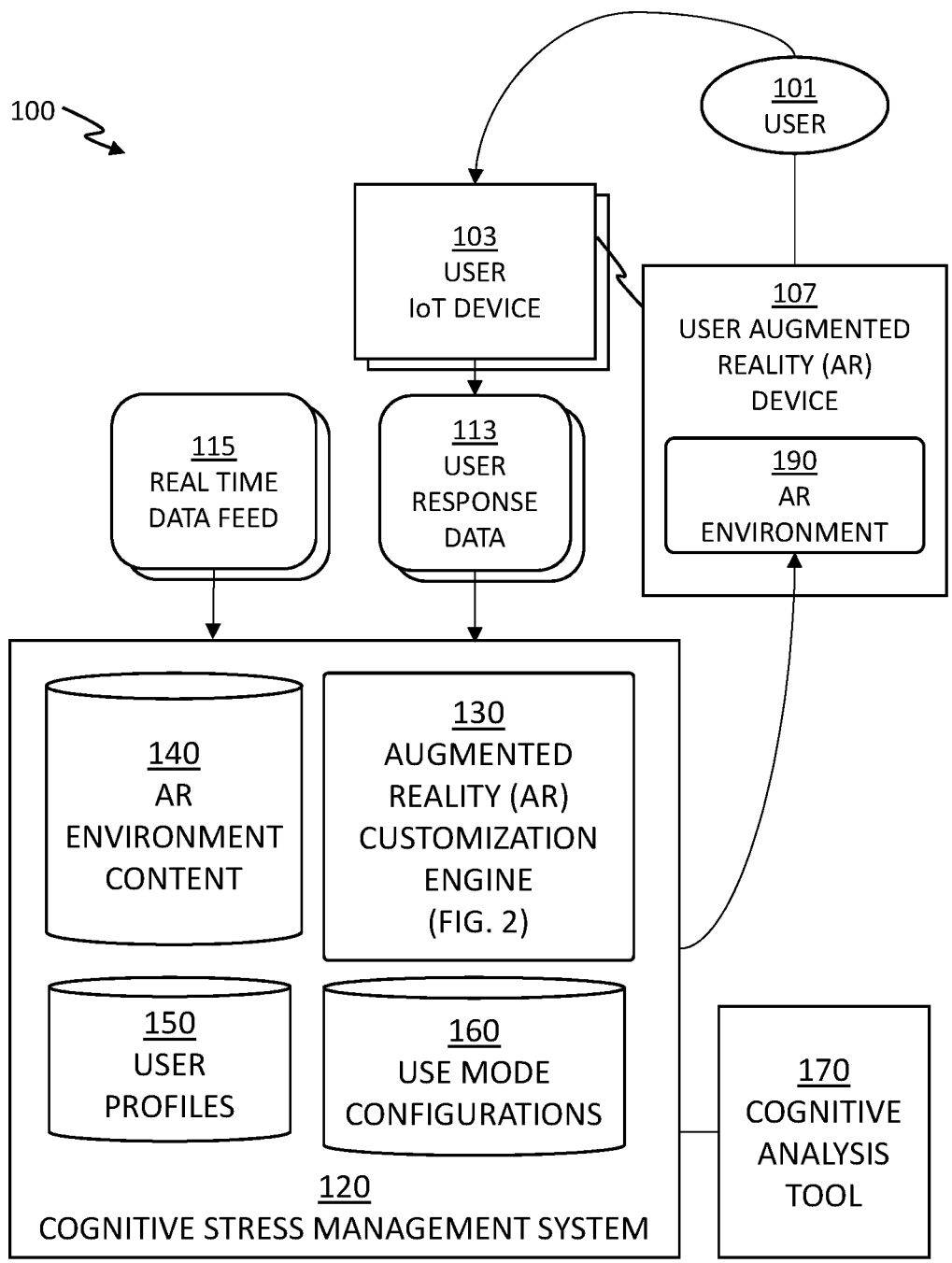
FIG. 1 depicts a system for cognitively managing stress by use of customized augmented reality (AR) environments, in accordance with one or more embodiments set forth herein.

FIG. 1 depicts a system 100 for cognitively managing stress by use of customized augmented reality (AR) environments, in accordance with one or more embodiments set forth herein.

Embodiments of the present invention recognizes that various psychological conditions and mental disorders may be alleviated by various therapies with respect to the level of stress associated with such conditions and disorders. People experience difficulty doing routine tasks when they are under stress. Also, causes of stresses are often difficult to identify due to complexity in the circumstances with respect to communication, relationships, and other reasons that are mostly private. In contexts of medical, educational, and law enforcement, properly identifying causes for stress on people and attaining certain intended level of stress in the same people in respective contexts would be improve individual health, educational development, as well as efficiency in investigations.

The reduction of stress in the embodiments of the present invention also allows for a person to become more comfortable executing a task because they have rehearsed that process in a controlled environment that started in a low stress environment and ended in an environment that match a target task execution environment. The embodiments of the present invention improve the rehearsal process and allow for the controlled change in a level of confidence which could not be completed by conventional rehearsal methods.

The system 100 includes a cognitive stress management system 120, which communicates with a user 101 via a user Augmented Reality (AR) device 107. The user AR device 107 processes and delivers an Augmented Reality (AR) environment 190 in which the user 101 can receive audio, visual, and any other sensory stimuli, as presented by the user AR device 107 as generated from the cognitive stress management system 120. One or more user Internet of Things (IoT) device 103 monitors stress levels of the user 101 by measuring various biometrics such as heart rate, blood pressure, perspiration, and certain stress hormone levels as configured for the cognitive stress management system 120. The one or more user IoT device 103 sends respective user response data 113 resulting from aforementioned monitoring to the cognitive stress management system 120, such that the cognitive stress management system 120 can adjust the AR environment 190 to induce a certain desired response from the user 101. Examples of the user IoT device 103 include, but are not limited to, various wearable biometric monitoring devices and/or sensors such as smartwatches, and audio/video capture and analysis in a certain location Embodiments of the present invention recognizes that latest Augmented Reality and/or Virtual Reality (AR/VR) technologies offers various user AR devices 107 that are commercially available for personal uses. Currently numerous hardware equipment of various capabilities are made available by many manufacturers. Examples of such AR/VR device, being used as the user AR device 107 in the embodiments of the present invention, include, but are not limited to, various wearable devices such as various headgears, smart glasses, and VR goggles, as well as a VR room equipped for AR environment delivery with interactive monitoring of the user responses.

The cognitive stress management system 120 receives one or more real time data feed 115 that may be utilized in generating the AR environment 190. The real time data feed 115 may be collected as specified by the user 101 in order to induce a specific type of psychological response, in accordance with particular use mode of the cognitive stress management system 120. For example, the user 101 have identified predetermined audience and/or participants as family members for a Rehearsal Mode. When the user 101 seeks calming effect in rehearsing for a public presentation, as in the Rehearsal Mode of the cognitive stress management system 120, the real time data feed 115 is, for example, an audio-visual response of the identified family members as being captured while the family members are viewing a practice run of the public presentation in the AR environment 190 by the user 101.

The cognitive stress management system 120 includes an Augmented Reality (AR) customization engine 130, AR environment content 140, user profiles 150, and use mode configurations 160. The cognitive stress management system 120 is coupled to one or more cognitive analysis tool 170 that would analyzes the user response data 113 based on purposes of respective use mode and a user profile corresponding to each user for which the AR environment 190 is customized. The AR customization engine 130 prepares and classifies the AR environment content 140 per user, per intended purposes, per stress effect on individual users, and many other ways relevant to the usage of the cognitive stress management system 120. Examples of the AR environment content 140 include, but are not limited to, still images and video clips of certain individuals with varying facial expressions and actions, particular locations, colors, and/or a certain sound such as recognizable voices and musical tunes. The preparation and classification of the AR environment content 140 are collectively referred to as curation. The AR customization engine 130 generates the AR environment 190 by augmenting and customizing the AR environment content 140 according to a specific use mode configuration corresponding to the purposes and intentions of the user 101. In augmenting the AR environment content 140, the AR customization engine 130 may employ certain cognitive analytics tools and AR/VR modeling tools.

The cognitive stress management system 120 is to achieve a set of goal responses with regard to stress levels of the user 101, respective to one or more use modes as configured in the respective use mode configurations 160. The goal responses are individually customized for each user and for each use mode, as each person can have different response in the stress level even to the same AR environment. The term "use mode" indicates a mode of operation for a particular purpose as performed by the cognitive stress management system 120 and the AR customization engine 130. Accordingly, the terms "use mode configuration" indicates a set of parameters configured to operate a corresponding use mode. For example, parameters of a specific use mode configuration, amongst a plurality of use mode configurations, includes, but is not limited to, a subject user profile to which the specific use mode is applicable, which content to present to a subject user, in how many levels and in what order, to achieve a purpose corresponding to the specific use mode.

Targeted stress levels for the user 101 in each use mode is specified according to respective purposes of the use modes and according to individual user profiles. The user 101 is associated with a unique baseline of stress levels for various stages of psychological status, which is represented in one of the user profiles 150 corresponding to the user 101.

The Augmented Reality (AR) customization engine 130 prepares the user AR device 107 and the user IoT device 103 in order to provide the AR environment 190 to the user 101. The AR customization engine 130 identifies a user profile from the user profiles 150 corresponding to the user 101 and determines a use mode and a goal response accordingly. The AR customization engine 130 selects a subset of the AR environment content 140 based on a use mode configuration for the determined use mode and the user profile, as well as the present status of the user response as monitored by the user response data 113 where applicable. The AR environment content 140 stores various visual images, still life and/or video clips, with or without associating audio files that would be element of the AR environment 190. The AR environment content 140 includes content customarily generated and/or provided by the user 101, as well as content collected from the public domain. The AR customization engine 130 validates if the selected AR environment content 140 is authorized for usage in the AR environment 190.

The AR environment content 140 is classified and presorted with respect to respective stress effects, either stress-inducing or stress-relieving, on the user 101, according to the user profile 150 and the use mode configurations 160. Also, even amongst the same stress effect on the user 101, the AR environment content 140 may be further sub-classified according to the intensity of the same stress effect. For example, if the user 101 has images of family members, friends, teachers, relatives, and other acquaintances associated with the stress-relieving effect, the AR customization engine 130 subclassifies the respective images based on the respective relationships and closeness of the individuals appearing in the images, respective facial expressions of the individuals appearing in the images, as well as descriptive nature of the images such as reactions by the individuals as an audience for a performance by the user 101 in the AR environment 190. By use of the cognitive analysis tool 170, the AR environment content 140 can be further analyzed by overall impression, circumstances, and color scheme of the respective images in order to refine the stress effect classification. The AR customization engine 130 selects such classified AR environment content 140 more effectively to attain goal responses on the user 101 by generating the AR environment 190 with so selected AR environment content 140. Also the AR customization engine 130 can create variations of certain images of the same stress effect for a varying degrees, based on past user responses, also referred to as the user history, as recorded in the user profile. The scale of varying degrees of the stress effects is determined based on the user profile, particularly in relation with the user history describing the past responses and the level of confidence in the AR environment 190 and the purposes of the respective use mode, and/or responsiveness to the AR environment 190 and effectiveness of the resulting goal responses on the user 101.

The AR customization engine 130 generates the AR environment 190 and sends the AR environment 190 to the user AR device 107, through which the user 101 experiences augmented reality of the AR environment 190. The user 101 responds to the AR environment 190 and various biometrics of the user 101 indicating in stress levels and/or psychological status of the user 101 are captured by the user IoT device 103 as the user response data 113. The AR customization engine 130 receives the user response data 113 from the user IoT device 103 and cognitively analyzes the user response data 113 by use of the cognitive analysis tool 170, to determine whether or not a goal response on the user 101 has been attained, according to the use mode configuration and the user profile of the user 101. The AR customization engine 130 resets baseline stress level and/or psychological status of the user 101 for generating another AR environment 190, in case where the goal response has not been attained. Details on operations of the AR customization engine 130 are presented in FIG. 2 and corresponding description.

The user profile 150 corresponding to the user 101 describes various individual characteristics of the user 101 in using the cognitive stress management system 120, including but not limited to: demographic information describing the user 101 including age, gender, ethnicity, occupation, and other psychologically meaningful classifications with respect to user response; condition relevant to individual stress response; a scale of stress levels and/or psychological states of the user 101 as quantified in various biometrics such as heart rate, blood pressure, perspiration, certain stress-related hormone levels, voice; any available user history data describing past records of the user 101 using the cognitive stress management system 120; and goal response ranges respective to use modes predefined in the use mode configurations 160 of the cognitive stress management system 120.

The cognitive analysis tool 170 indicates one or more cognitive analytics tool to analyze, learn, and, contextualize the AR environment 190 and the user response data 113 in order to produce goal responses respective to the use mode configurations 160 and the user profile 150. Even when the AR customization engine 130 performs in the same use mode with the same initial configuration, individual users can have distinctive responses to presented AR environment 190. Accordingly, because a range of goal response corresponding to the use mode is different from one user to another, the AR customization engine 130 interprets the user response data 113 based on a user-specific standard and determines a range of user-specific goal responses, by use of the cognitive analysis tool 170. The cognitive analysis tool 170 may be proprietary for the cognitive stress management system 120 and/or may be selected from commercially available cognitive analytics tools that are offered to the public for a fee.

Figure 2:
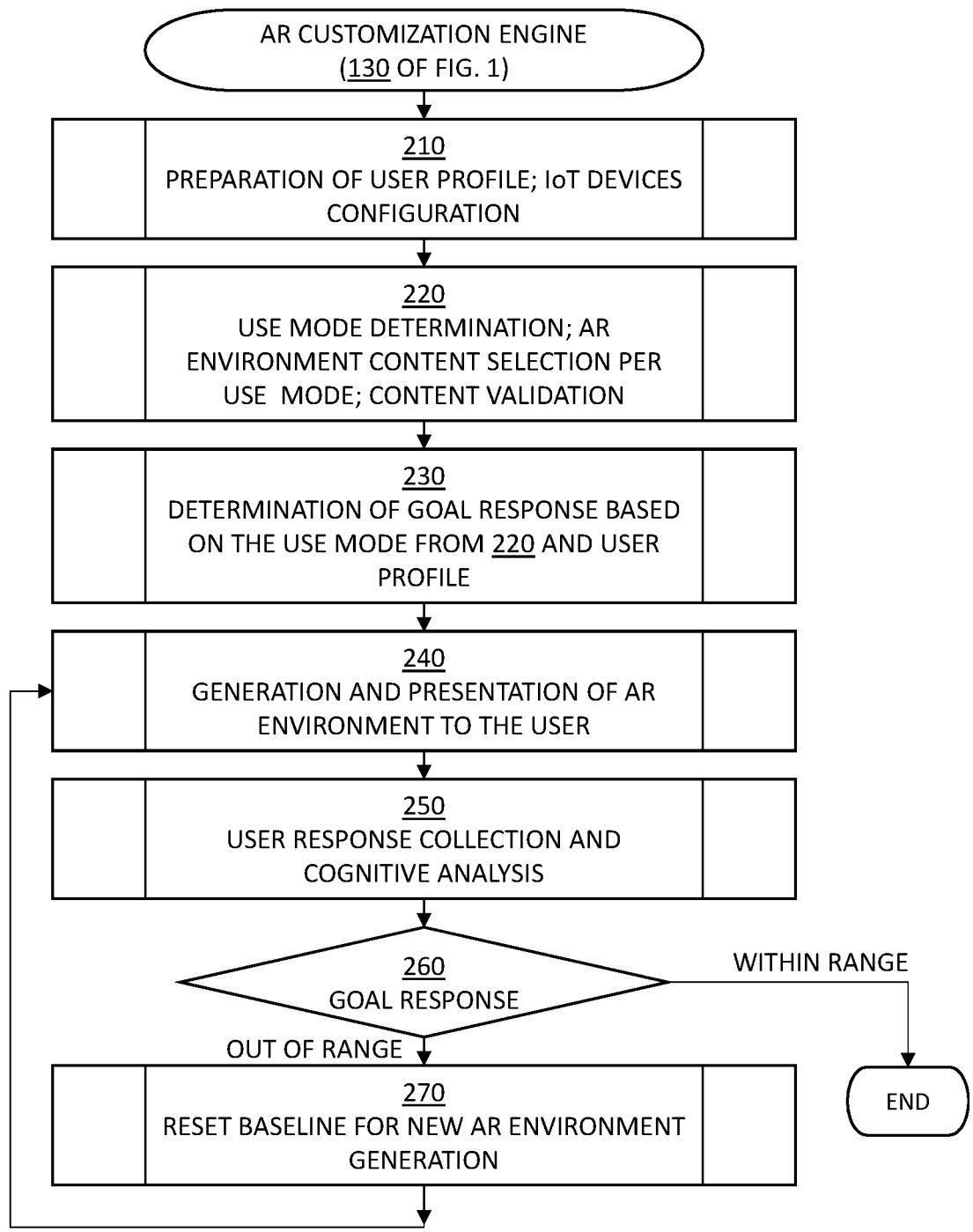
FIG. 2 depicts a flowchart of operations performed by the Augmented Reality (AR) customization engine, in accordance with one or more embodiments set forth herein.

FIG. 2 depicts a flowchart of operations performed by the Augmented Reality (AR) customization engine 130, in accordance with one or more embodiments set forth herein In block 210, the AR customization engine 130 prepares the user profile 150 corresponding to the user 101 who receives the AR environment 190, in order to customize the AR environment 190. The user profile 150 of the user 101 includes individual data describing the user 101 with respect to the usage of the cognitive stress management system 120. Examples of data elements in the user profile 150 include, but are not limited to, demographic information of the user 101 including age, gender, ethnicity, occupation, and other psychologically meaningful classifications corresponding to the user 101; condition relevant to individual stress response of the user 101; an average stress level and/or psychological status of the user 101 as quantified in various biometrics such as heart rate, blood pressure, perspiration, certain stress-related hormone levels, voice, which would be utilized to configure individual goal responses per respective use mode of the cognitive stress management system 120; any available user history data describing past records of the user 101 using the cognitive stress management system 120; and customized goal response ranges for the user 101, respective to use modes predefined in the use mode configurations 160 of the cognitive stress management system 120.

The AR customization engine 130 also configures the user IoT device 103 to transfer the user response data 113. The user IoT device 103 is configured to monitor biometrics of the user 101 and captures and transfers responses by the user 101 as measured in biometric quantities to the AR customization engine 130. The user IoT device 103 and the user AR device 107 have a communication channel to map timelines of responses by the user 101 to the progress of the AR environment 190, such that the AR customization engine 130 can distinguish respective responses in the user response data 113, as corresponding to a certain point in time and/or distinctive snapshots of the AR environment 190. Then the AR customization engine 130 proceeds with block 220.

In certain embodiments of the present invention, an agent of the cognitive stress management system 120, as customized for the user 101, is implemented in the user AR device 107, and the AR customization engine 130 operates remotely as being coupled via a communication channel. The user IoT device 103 includes, but not limited to, any wearable and/or other personal devices on the user 101 for measuring biometrics, microphones and/or camera that can capture voice and facial expression of the user 101. The user IoT device 103 and the user AR device 107 can be integrated in one physical device or a coordinated set of devices, in order to capture the user response more effectively as the user 101 immerses in AR environment 190.

In block 220, the AR customization engine 130 determines the use mode of the cognitive stress management system 120, and selects a subset of the AR environment content 140 according to the determined use mode and the user profile 150 as prepared in block 210. The AR customization engine 130 subsequently validates the selected subset of the AR environment content 140, by determining whether or not the selected AR environment content 140 is authorized for use in generating the AR environment 190 for the user 101. Then the AR customization engine 130 proceeds with block 230.

In certain embodiments of the present invention, one or more use mode of the cognitive stress management system 120 is predefined in the use mode configurations 160. In determining the use mode, the AR customization engine 130 utilizes inputs from an administrator and/or the user 101 via a user interface. Few examples of the use modes, for which use mode configurations corresponding to each use mode are predefined in the use mode configurations 160, includes Rehearsal mode, Stress Relief mode, and Investigation mode. The Rehearsal mode is for the user 101 to be at ease in certain Details on the exemplary use mode configuration are presented in FIG. 3 and corresponding description.

As noted, the use mode of the cognitive stress management system 120 indicates a mode of operation for a particular purpose, and accordingly, the use mode is determined based on why the AR environment 190 is provided for the user 101. Embodiments of the present invention recognizes that various psychological therapy techniques such as flooding and/or graded exposure are currently available in conventional therapy sessions. With the cognitive stress management system 120, such psychological therapy can be performed more effectively based on dynamic feedback of the user response data 113 that is being captured by the user IoT device 103 as the user 101 experiences the AR environment 190. The AR customization engine 130 generates the AR environment 190 according to customized response factors including the user history and stress baseline of the user profile 150, as applied by the use mode configuration 160. Further, the AR customization engine 130 offers the AR environment 190 that is customized for the user 101, by using private/custom AR environment content and by dynamically applying individual baseline of the user 101 in repeated runs of the AR environment generation. The AR customization engine 130 also customizes production of the AR environment 190 by flexibly adjusting a use mode configuration of a particular use mode, according to various characteristics of the user profile of the user 101. For example, the AR environment content 140 includes a picture of a close family member A, but the user profile of the user 101 indicates that the close family member A had passed recently. The AR customization engine 130 then filters out the picture of A from generating the AR environment 190 in use modes that intend to relieve stress.

In certain embodiments of the present invention, the AR customization engine 130 offers an on-line mode and an off-line mode for applicable use mode configuration, in order to increase availability of the cognitive stress management system 120 even where a communication channel such as a Wi-Fi connection for the real time data feed 115 is not provided. For example, in the off-line mode of the Rehearsal mode configuration, the AR customization engine 130 selects preconfigured still images and/or video loop previously recorded from the real time data feed 115, as stored in the AR environment content 140 to generate the AR environment 190. Whereas in the on-line mode of the same Rehearsal mode configuration, the AR customization engine 130 selects the real time data feed 115 that captures live reactions of preselected participants to performances by the user 101 in the AR environment 190. The AR customization engine 130 can be configured to automatically select either the on-line or the off-line option of applicable use mode configuration, according to the communication channel status while preparing for the selected use mode configuration.

In certain embodiments of the present invention, the AR customization engine 130 validates the selected AR environment content 140 for authorization to use, by checking if the AR environment content 140 is a public domain content, a custom content provided by the user 101, a type of permission provided by an author of the AR environment content 140, and authorization to respective users of the cognitive stress management system 120. The AR customization engine 130 checks whether or not the selected AR environment content 140 is a copyrighted material, and if a proper authorization has been acquired for any copyrighted material and/or from identifiable people appearing in the AR environment content 140. In certain other embodiments of the present invention, the AR customization engine 130 checks whether or not the selected AR environment content 140 is a private material provided by the user 101 that can be utilized only for the AR environment 190 to the user 101, or the user 101 gave permission to use the material stored in the AR environment content 140 in generating other AR environments for other users. In certain embodiments of the present invention, the AR customization engine 130 can further associate individuals appearing in images/sounds of the AR environment content 140 with respective relationships with the user 101, in order to analyze the changes in the stress level on the user 101 when such images/sounds are presented in the AR environment 190. In certain other embodiments of the present invention, the AR customization engine 130 can build the AR environment content 140 by collecting materials only from the public domain or otherwise licensed content, and keep private AR environment content in user profiles respective to users only for individual use.

In block 230, the AR customization engine 130 determines a goal response by the user 101 based on the use mode configuration corresponding to the use mode determined in block 220 and baseline biometrics of the user 101 as specified in the user profile 150 corresponding to the user 101. In certain embodiments of the present invention, the AR customization engine 130 defines the goal response relative to the baseline biometrics of the user 101 focusing on recognizing the effect of the AR environment 190 on the user 101, by comparing the baseline biometrics with the user response data 113. Then, the AR customization engine 130 proceeds with block 240.

Blocks 240 through 270 are performed as a unit of iteration for generating each AR environment. When a goal response corresponding to the user mode configuration and the user profile is attained by a current AR environment, as determined from block 260 based on the cognitive analysis from block 250, then the AR customization engine 130 stops generating further AR environment.

In block 240, the AR customization engine 130 generates the AR environment 190 by use of the selected subset of the AR environment content 140 based on the use mode configuration and subsequently sends the generated AR environment 190 to the user AR device 107, such that the user 101 experiences the generated AR environment 190 by use of the AR device 107. Then, the AR customization engine 130 proceeds with block 250.

In certain embodiments of the present invention, the AR customization engine 130 checks the initial status of the user 101 prior to present the generated AR environment 190 to ascertain that the baseline biometrics of the user 101 is aligned with the baseline intended in the generated AR environment 190. If the AR customization engine 130 determines that the user 101 is to be in a certain initial status with less stress than observed via the user IoT device 103, then the AR customization engine 130 can, for example, pause and let the user 101 rest for a while, instruct the user 101 to take deep breaths along with presenting a peaceful landscapes, favorite places of the user 101, smiling faces of close friends of the user 101, or any other calming images and/or sounds customarily set for the user 101 and/or generic images that had been effective for the user 101 in the past as recorded in the user profile 150.

In certain embodiments of the present invention, the AR customization engine 130 can send the use mode configuration specifying the order and durations of how the AR environment 190 should progress and a selected subset of the AR environment content 140 to the user AR device 107, such that the AR environment 190 can be generated remotely on the user AR device 107. In the same embodiments of the present invention, loading the selected subset of the AR environment content 140 to the user AR device 107 is deemed as generating the AR environment 190 by the AR customization engine 130 as the AR customization engine 130 facilitates and enables generation of the AR environment 190 on the user AR device 107 for the user 101. Particularly where the user AR device 107 should operate off-line, such pre-loaded images and the use mode configurations facilitating off-line AR environment 190 would maximize effectiveness of the cognitive stress management system 120 in use modes where the real time data feed 115 is optional. By using an agent of the cognitive stress management system 120 on the user AR device 107, the AR environment 190 can still be repeatedly adjusted in blocks 240 through 270 while operating off-line.

In block 250, the AR customization engine 130 collects the user response data 113 sent from the user IoT device 103 and cognitively analyzes the received user response data 113 in order to determine whether or not the user response data 113 coincides with the goal response for the user 101 in the current use mode as determined in block 230. The AR customization engine 130 invokes the cognitive analysis tool 170 that is be proprietary to the cognitive stress management system 120 or commercially available. Then the AR customization engine 130 proceeds with block 260.

In certain embodiments of the present invention, the AR customization engine 130 continuously monitors the user response data 113 for a certain predefined period of time and/or until a certain threshold stress level change is detected, prior to determining if the goal response has been attained on the user 101 in block 260. As noted, the user IoT device 103 forwards the user response data 113 as the user 101 experiences the AR environment 190 as presented in block 240.

In certain embodiments of the present invention, the AR customization engine 130 identifies stress level changes on the user 101 from the user response data 113, and correlates the identified stress level changes with changes in the AR environment 190, based on the baseline biometrics and the previous AR environment where applicable. By cognitively analyzing the stress level changes and the changes in the AR environment, the AR customization engine 130 identifies a stressor for the user 101, which is further utilized on purposes respective to the use modes. For example, in the Investigation mode, identifying the stressor for the user 101 can be critical to resolve any societal/psychological issues of the user 101, particularly where the user 101 is resistant to communicating how and why the user 101 suffers from a certain stress, as in the cases of abusive and unequal relationships.

In block 260, the AR customization engine 130 determines whether or not the user response data 113, which captures the user 101 responding to the AR environment 190 presented in block 240, is within a threshold range of the goal response determined in block 230. If the AR customization engine 130 determines that the user response data 113 is within the threshold range of the goal response according to the use mode configuration and user profile, then the AR customization engine 130 terminates as no further AR environment is to be generated. If the AR customization engine 130 determines that the user response data 113 to the AR environment 190 is out of the threshold range of goal response set for the user 101 according to the use mode configuration, then the AR customization engine 130 proceeds with block 270.

As noted, in certain embodiments of the present invention, the AR customization engine 130 defines the goal response relative to the baseline biometrics of the user 101. The AR customization engine 130 compares the baseline biometrics of the user 101 before the user 101 experiences the AR environment 190 and the user response data 113 from block 250. The user response data 113 includes another biometrics of the user 101 as responding to the AR environment 190 that had been presented in presented in block 240. By comparing the baseline biometrics of the user 101 prior to the AR environment 190 and the user response data 113 responding to the AR environment 190, the AR customization engine 130 detects the changes from the baseline biometrics to the user response data 113, and interprets the amount of changes in respective elements of the biometrics of the user 101 as elements of the goal response. The AR customization engine 130 cognitively analyzes the amount of changes in certain biometrics element as an increased or a decreased level of stress, a more agitated or a more relaxed psychological status, as being customized for the user 101, because effect of stimuli presented in the AR environment 190 on individual users may vary from person to person.

In block 270, the AR customization engine 130 resets the baseline biometrics of the user 101 according to the user response data 113 obtained in block 250, because the user 101 is not demonstrating the goal response set in block 230 upon being presented with the AR environment 190 from block 240. The AR customization engine 130 resets the baseline biometrics of the user 101 to mark a stress level/ psychological status prior to present another AR environment 190. The AR customization engine 130 records the baseline biometrics respective to the AR environments, in order to select the AR environment content for generating a next AR environment in block 240, and to keep user history data in the user profile. Then the AR customization engine 130 loops back to block 240.

In certain embodiments of the present invention, the AR customization engine 130 adjusts the baseline biometrics of the user 101 based on the user history of past responses in the user profile 150 as well as the user response data 113 from block 250. Where a specific AR environment content, including but not limited to images of a certain individual, particular locations, colors, and/or a certain sound such as recognizable voices and musical tunes, has respective records of a certain psychological effect on the user 101 in the user profile 150, then the AR customization engine 130 adjusts and/or resets the baseline biometrics in order to select and apply such AR environment content corresponding to desired effect, that is converging to the goal response of the use mode, in generating the next AR environment 190. Conversely, the AR customization engine 130 adjusts and/or resets the baseline biometrics to omit any AR environment content which causes any responses on the user 101 diverging from the goal response of the use mode, in preparation of block 240 for generating the next AR environment 190.

Figure 3:
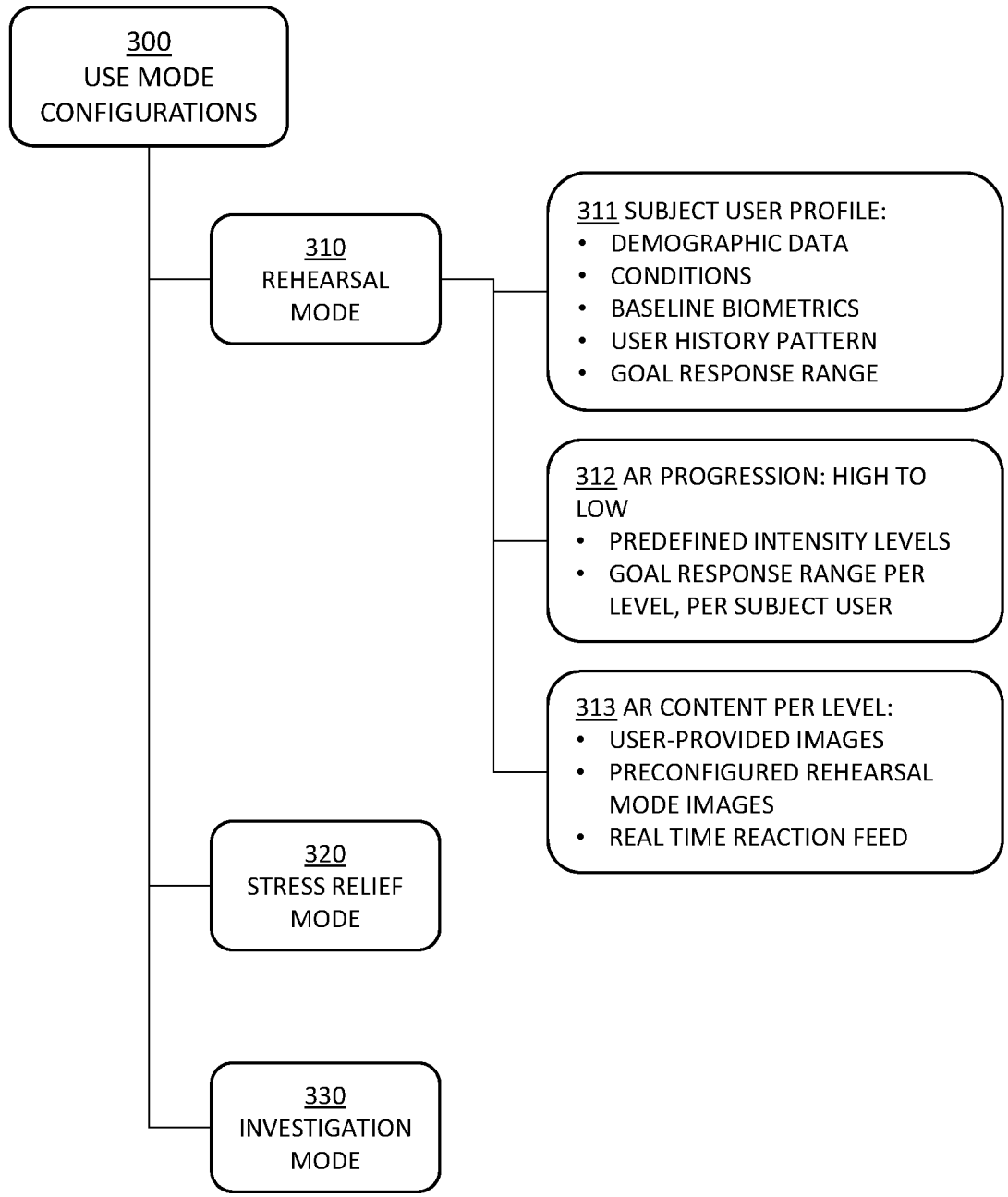
FIG. 3 depicts exemplary use mode configurations predefined in the cognitive stress management system, in accordance with one or more embodiments set forth herein.

FIG. 3 depicts exemplary use mode configurations 300 predefined in the cognitive stress management system 120, in accordance with one or more embodiments set forth herein.

The exemplary use mode configuration 300 is an instance of the use mode configuration 160 of the cognitive stress management system 120. In the exemplary use mode configurations 300, a Rehearsal mode 310, a Stress Relief mode 320, and an Investigation mode 330 are specified. All use mode configurations 310, 320, and 330 are similarly structured with components including, but not limited to, a subject user profile, an Augmented Reality (AR) progression, and AR content per level.

Objectives of the Rehearsal mode 310 is to attain composure and to improve performance for a certain exercise/ event. The Rehearsal mode 310 includes the subject user profile 311 that describes various characteristics of users that can benefit from using the cognitive stress management system 120 in the Rehearsal mode 310. The characteristics of the users specified in the subject user profile 311 of the use mode configuration 300 for the Rehearsal mode 310 includes, but are not limited to, demographic information of the users including age, gender, ethnicity, occupation, and other psychologically meaningful classifications. The subject user profile 311 for the Rehearsal mode 310 further includes conditions applicable to the users of the Rehearsal mode 310, such as stage fright, extreme shyness, a lack of experiences, and/or other types of phobia relevant to the public setting and performances in public. The subject user profile 311 for the Rehearsal mode 310 also includes a range of baseline biometrics applicable to the type of users, respective to certain age groups in the users, or based on a specific instance of a user profile for a candidate user. The subject user profile 311 for the Rehearsal mode 310 further includes user history patterns applicable for the Rehearsal mode 310 such that the cognitive stress management system 120 can learn the correlation between the user history and the effectiveness of the AR environments running in the Rehearsal mode 310 in achieving composure and in improving performances in public settings. The subject user profile 311 for the Rehearsal mode 310 also includes goal response ranges respective a certain age group and/or individual users.

An AR progression 312 for the Rehearsal mode 310 includes, but not limited to, predefined intensity levels respective to each AR environment, a range of goal response with respect to stress measurements per intensity levels in the Rehearsal mode 310, customized for a certain age group and/or individual users.

An AR content per level 313 for the Rehearsal mode 310 includes, but not limited to, user-provided images, images preconfigured for rehearsal mode, and real-time reaction feed from preselected participants for the individual users in on-line mode.

For example, User A is a student in elementary school preparing for a talk at a school concert for other students and parents. Because User A is nervous and afraid of standing in front of such an audience, User A can benefit from practicing the talk in AR environments running in the Rehearsal mode 310. In order to facilitate the exercise, the family of User A provided certain family photos with a permission to add it to the AR environment content 140 for further use, and further offered to participate in viewing the performance in the AR environment by User A and to give real-time feedback. User A performs the talk while wearing a VR goggle presenting the family photos as a first AR environment. Once the stress level of User A drops to normal during the performance, then User A performs in another AR environment with real-time feedback from the family, and the stress levels imposed on the AR environments gradually increases to, for example, an image of an empty auditorium, and to an image of audiences in the auditorium. The goal response would be a normal stress level for User A while performing the talk in the AR environment simulating the audiences in the auditorium, such that User A would perform at the school concert with ease.

Objectives of the Stress Relief mode 320 is to attain a decreased level of stress on the intended individuals respective to particular contexts, such that the individuals can recover a certain normalcy and/or can perform a certain act that would have been difficult due to a high level of stress without the AR environment exercise. The subject user profile for the Stress Relief mode 320 includes, but are not limited to, an Alzheimer's patient, a victim of a violent crime, and a person with anxiety disorder.

For example in the Stress Relief mode 320, User B is suffering from Alzheimer's disease but needs to move to a new place by necessity. In order to relieve stress caused by the move and/or the disease, User B can have a daily session with an AR environment presenting a previous home and old neighborhood of User B, departed and/or remote family members of User B, and similar images and sounds that are familiar to User B and are known to have a calming effect on User B, as recorded in the user profile of User B. The goal response is a stress level less than or equal to an average-normal stress level of User B.

For another example in the Stress Relief mode 320, User C is a victim of and/or a witness to a violent crime and, immediately after the crime, User C is hesitant and/or otherwise unable to talk with police officers due to the high stress level. In order to relieve stress caused by the crime, User C is initially presented with an AR environment presenting favorite places of User C with calming effect, and then the AR environment gradually migrates to the pictures of the scene of the crime. The goal response is a stress level low enough for User C to talk with the police officers.

For still another example in the Stress Relief mode 320, User D is suffering from an anxiety disorder but needs to move to a new place by necessity. In order to adapt to the new place with less anxiety outbreak, User D views an AR environment presenting a favorite space in the new place and a favorite shop in a new neighborhood as needed, before the moving date. The goal response is a stress level lower than an average anxiety attach level when being reminded of the new place.

Objectives of the Investigation mode 330 is to identify a stressor, being observed as an increased stress level corresponding to changes in the AR environment. The subject user profile for the Investigation mode 330 may include, but are not limited to, a person who is showing behavioral problems but has difficulty communicating the cause of such problems with anyone who can help.

For example in the Investigation mode 330, User E is a student whose grade has recently plummeted but refuses to talk with parents. In order to find out why, upon request by the parents and/or according to recommendation from a school counselor, User E is presented with a series of AR environments simulating classes of User E with the AR environment content captured from class video monitoring system, presenting family members, social groups, and any person contacting User E. The goal response is an abrupt change in the stress level less of User E, as being mapped with changes in the AR environment content, in order to identify the stressor to User E.

Certain embodiments of the present invention offers various technical computing advantages, including the use of cognitive computing tools for automatically regenerating another custom Augmented Reality (AR) environment based on individual user response to a previously presented AR environment. Certain embodiments of the present invention offer automatically and comprehensively establishing, validating, and curating AR environment content for each user according to the objectives of the use mode as well as user history recording past responses to AR environments by each user. Certain embodiments of the present invention also improves a user interface of augmented reality (AR) device user interfaces by interactively generating, adjusting, and/or modifying AR environments in real time based on user responses to a previously presented AR environment, in order to achieve a certain goal response on the user. Certain embodiments of the present invention are implemented by use of a cloud platform/data center in various types including a Software-as-a-Service (SaaS) for the AR customization engine, Platform-as-a-Service (PaaS) for the cognitive stress management system, Database-as-a-Service (DBaaS) for the AR environment content, the user profiles, and the use mode configurations, and combinations thereof based on types of subscription. The cognitive stress management service is provided for subscribed business entities in need, such as educational, medical, social service, and/or law enforcement organizations, from any location in the world.

Figure 4:
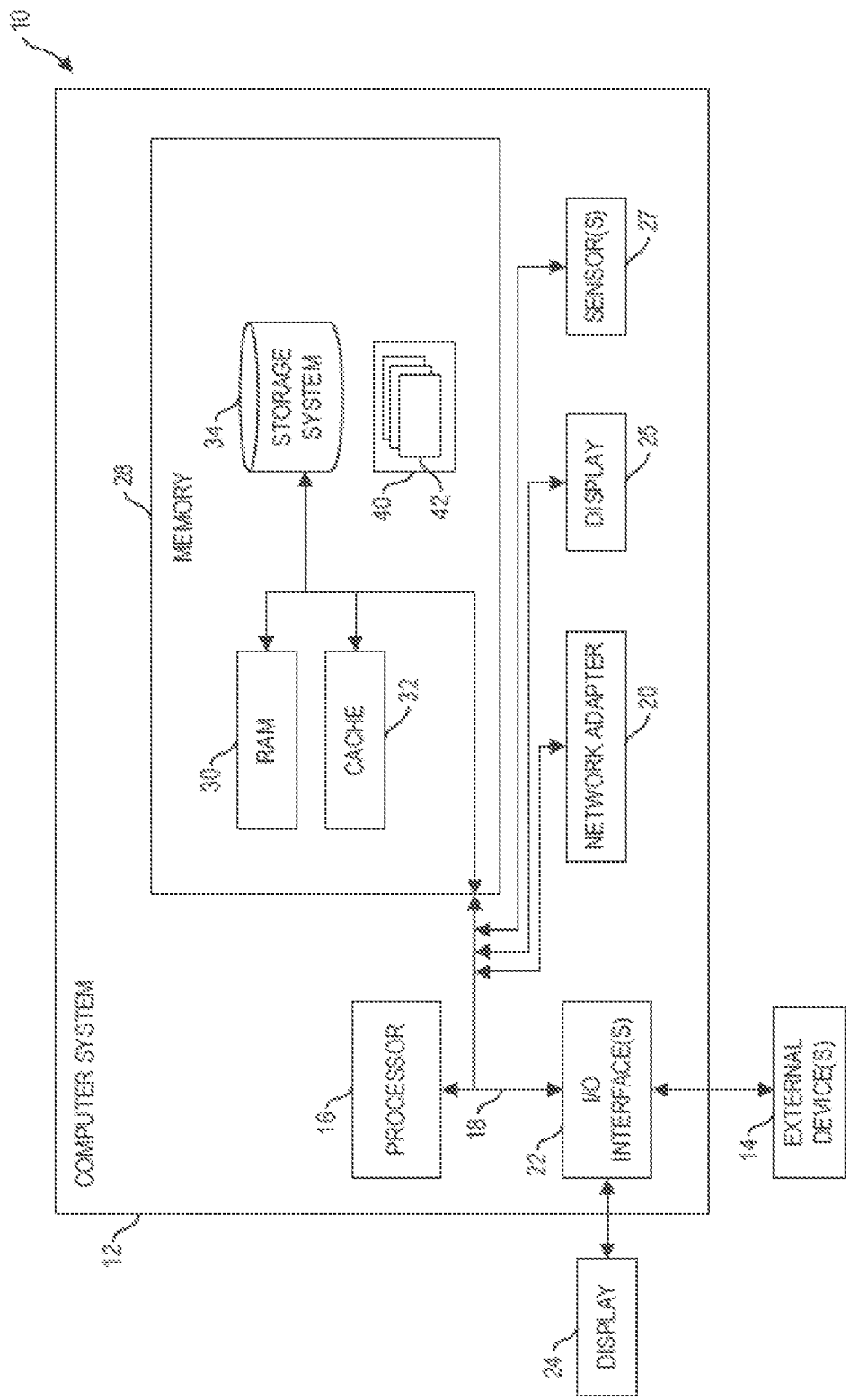
FIG. 4 depicts a cloud computing node according to an embodiment of the present invention.
Figure 5:
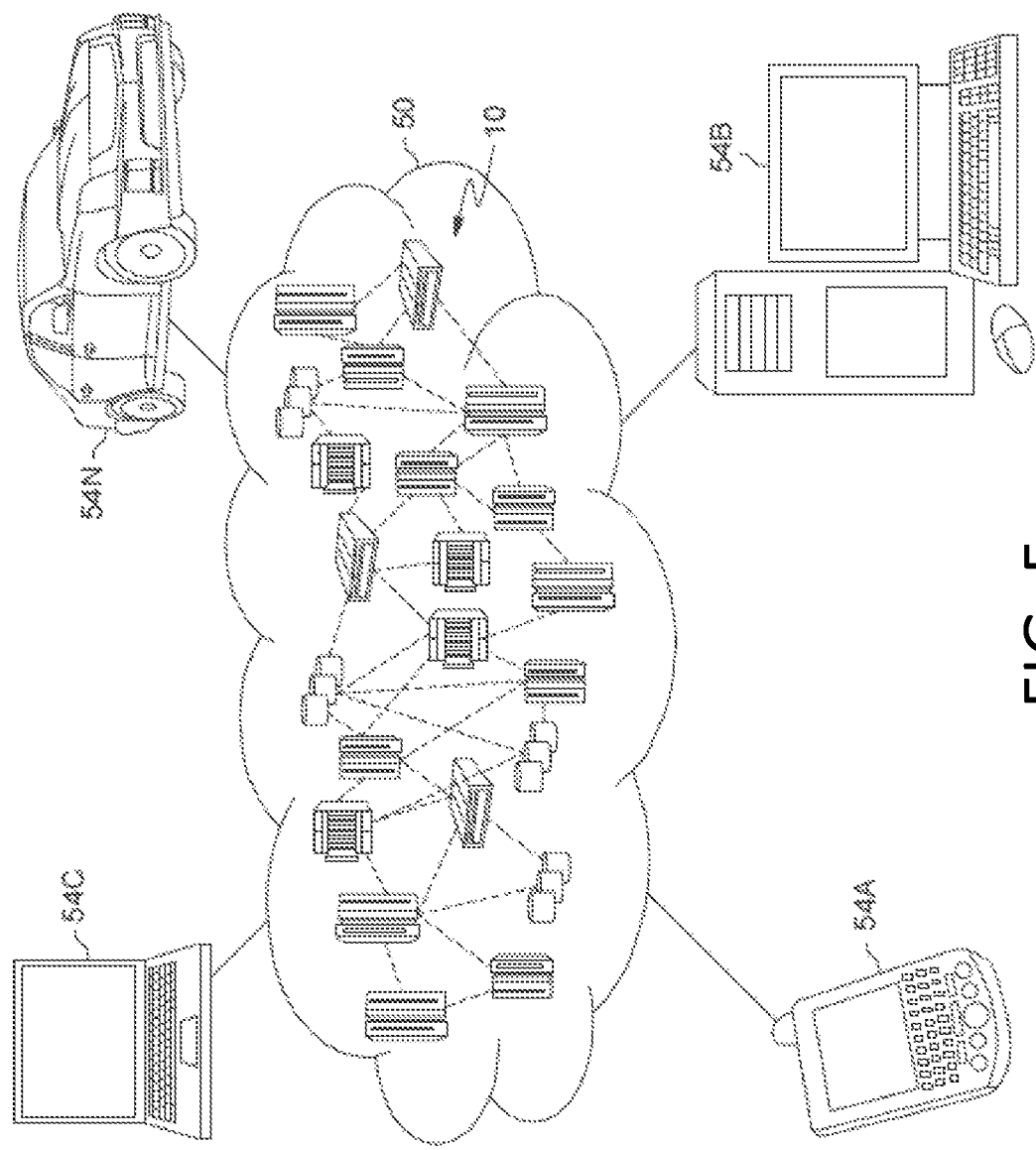
FIG. 5 depicts a cloud computing environment according to an embodiment of the present invention.
Figure 6:
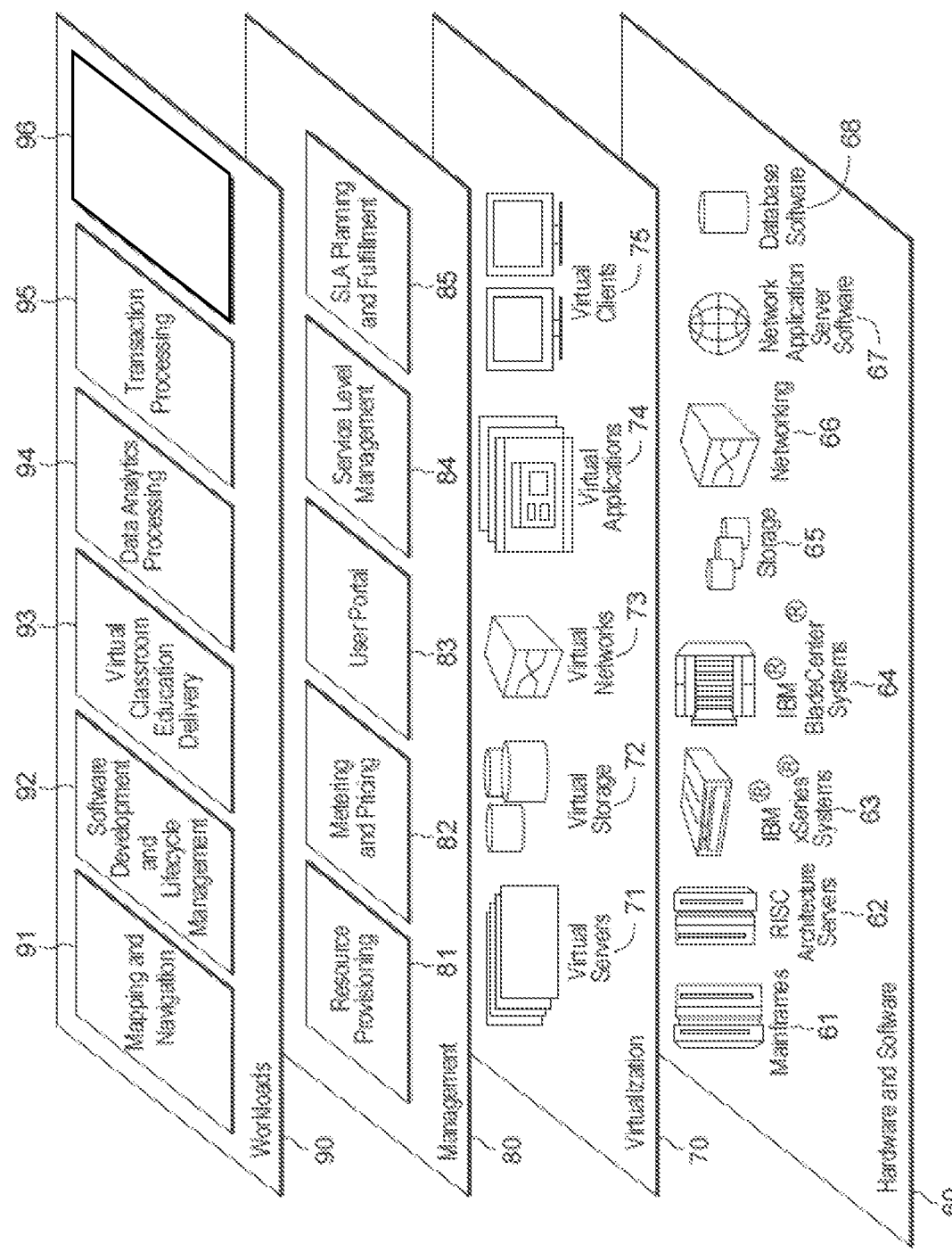
FIG. 6 depicts abstraction model layers according to an embodiment of the present invention.

FIGS. 4-6 depict various aspects of computing, including a cloud computing system, in accordance with one or more aspects set forth herein.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 4, a schematic of an example of a computer system/cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system 12, which is operational with numerous other general purpose or special purpose computing system environments or configurations. Examples of well-known computing systems, environments, and/or configurations that may be suitable for use with computer system 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 12 may be described in the general context of computer system-executable instructions, such as program processes, being executed by a computer system. Generally, program processes may include routines, programs, objects, components, logic, data structures, and so on that perform particular tasks or implement particular abstract data types. Computer system 12 may be practiced in distributed cloud computing environments where tasks are performed by remote processing devices that are linked through a communications network. In a distributed cloud computing environment, program processes may be located in both local and remote computer system storage media including memory storage devices.

As shown in FIG. 4, computer system 12 in cloud computing node 10 is shown in the form of a general-purpose computing device. The components of computer system 12 may include, but are not limited to, one or more processors 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 12 typically includes a variety of computer system readable media. Such media may be any available media that is accessible by computer system 12, and it includes both volatile and non-volatile media, removable and non-removable media.

System memory 28 can include computer system readable media in the form of volatile memory, such as random access memory (RAM) 30 and/or cache memory 32. Computer system 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile memory device (e.g., a "thumb drive", "external hard drive"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program processes that are configured to carry out the functions of embodiments of the invention.

One or more program 40, having a set (at least one) of program processes 42, may be stored in memory 28 by way of example, and not limitation, as well as an operating system, one or more application programs, other program processes, and program data. Each of the operating system, one or more application programs, other program processes, and program data or some combination thereof, may include an implementation of the cognitive stress management system 120 and the Augmented Reality (AR) customization engine 130 of FIG. 1, respectively. Program processes 42, as in the AR customization engine 130 and the cognitive stress management system 120, generally carry out the functions and/or methodologies of embodiments of the invention as described herein.

Computer system 12 may also communicate with one or more external devices 14 such as a keyboard, a pointing device, a display 24, etc.; one or more devices that enable a user to interact with computer system 12; and/or any devices (e.g., network card, modem, etc.) that enable computer system 12 to communicate with one or more other computing devices. Such communication can occur via Input/Output (I/O) interfaces 22. Still yet, computer system 12 can communicate with one or more networks such as a local area network (LAN), a general wide area network (WAN), and/or a public network (e.g., the Internet) via network adapter 20. As depicted, network adapter 20 communicates with the other components of computer system 12 via bus 18. It should be understood that although not shown, other hardware and/or software components could be used in conjunction with computer system 12. Examples, include, but are not limited to: microcode, device drivers, redundant processors, external disk drive arrays, RAID systems, tape drives, and data archival storage systems, etc.

Referring now to FIG. 5, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and processing components for the stress management services as provided by the cognitive stress management system 96, as described herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description set forth herein has been presented for purposes of illustration and description, but is not intended to be exhaustive or limited to the form disclosed. Many modifications and variations will be apparent to those of ordinary skill in the art without departing from the scope and spirit of the disclosure. The embodiment was chosen and described in order to best explain the principles of one or more aspects set forth herein and the practical application, and to enable others of ordinary skill in the art to understand one or more aspects as described herein for various embodiments with various modifications as are suited to the particular use contemplated.

What is claimed is:

1. A computer implemented method for cognitively managing a stress level on a user, comprising:

preparing, by one or more processor, a user profile corresponding to the user, the user profile including baseline biometrics for the stress level on the user and conditions affecting the stress level on the user in responding to one or more augmented reality (AR) environment, as delivered by a user AR device, and responses by the user to the one or more AR environment being monitored by one or more Internet of Things (IoT) device configured for the user;

determining, by the one or more processor, a use mode for the one or more AR environment, wherein the use mode corresponds to a use mode configuration specifying how to generate the one or more AR environment for the user to attain purposes of the use mode;

selecting, by the one or more processor, AR environment content for the one or more AR environment based on the user profile and the use mode, wherein the AR environment content includes audio-visual contents curated for respective stress effects to the stress level on the user;

determining, by the one or more processor, a goal response for the user as being presented with the one or more AR environment, based on the user profile and the use mode;

generating, by the one or more processor, an AR environment of the one or more AR environment by use of the AR environment content from the selecting according to the use mode configuration; and sending, by the one or more processor, the AR environment resulted from the generating to the user AR device for the user to experience the AR environment.

2. The computer implemented method of claim 1, further comprising:

obtaining the responses by the user to the AR environment from the one or more IoT device; and ascertaining, by use of one or more cognitive analysis tool, that the responses resulted from the obtaining are within a range of the goal response corresponding to the use mode.

3. The computer implemented method of claim 1, further comprising:

obtaining the responses by the user to the AR environment from the one or more IoT device;

ascertaining, by use of one or more cognitive analysis tool, that the responses resulted from the obtaining are out of a range of the goal response corresponding to the use mode;

resetting the baseline biometrics indicating the stress level on the user according to the responses; and generating a new AR environment of the one or more AR environment according to the use mode configuration, wherein the new AR environment is devised to induce another response closer to the range of the goal response than the responses to the AR environment.

4. The computer implemented method of claim 1, the selecting comprising:

validating the AR environment content for authorization to use, by checking if the AR environment content is a public domain content, a custom content provided by the user, a type of permission provided by an author of the AR environment content, and authorization applicable to respective users including the user.

5. The computer implemented method of claim 1, wherein the user profile includes demographic information of the user that may be utilized for psychologically meaningful classifications with respect to user response, conditions relevant to individual stress response of the user, a scale of stress levels on the user corresponding to respective biometrics measurements, and user history.

6. The computer implemented method of claim 1, wherein the use mode is selected from a Rehearsal mode, a Stress Relief mode, an Investigation mode, and wherein the use mode may operate either on-line or off-line.

7. The computer implemented method of claim 6, wherein the use mode is the Rehearsal mode operating on-line, the AR environment content includes a real-time data feed from one or more preselected participant reacting to a performance by the user in the AR environment.

8. A computer program product comprising:
a non-transitory computer readable storage medium readable by one or more processor and storing instructions for execution by the one or more processor for performing a method for cognitively managing a stress level on a user, comprising:
preparing a user profile corresponding to the user, the user profile including baseline biometrics for the stress level on the user and conditions affecting the stress level on the user in responding to one or more augmented reality (AR) environment, as delivered by a user AR device, and responses by the user to the one or more AR environment being monitored by one or more Internet of Things (IoT) device configured for the user;
determining a use mode for the one or more AR environment, wherein the use mode corresponds to a use mode configuration specifying how to generate the one or more AR environment for the user to attain purposes of the use mode;
selecting AR environment content for the one or more AR environment based on the user profile and the use mode, wherein the AR environment content includes audio-visual contents curated for respective stress effects to the stress level on the user;
determining a goal response for the user as being presented with the one or more AR environment, based on the user profile and the use mode;
generating an AR environment of the one or more AR environment by use of the AR environment content from the selecting according to the use mode configuration; and
sending the AR environment resulted from the generating to the user AR device for the user to experience the AR environment.

9. The computer program product of claim 8, further comprising:
obtaining the responses by the user to the AR environment from the one or more IoT device; and
ascertaining, by use of one or more cognitive analysis tool, that the responses resulted from the obtaining are within a range of the goal response corresponding to the use mode.

10. The computer program product of claim 8, further comprising:
obtaining the responses by the user to the AR environment from the one or more IoT device;
ascertaining, by use of one or more cognitive analysis tool, that the responses resulted from the obtaining are out of a range of the goal response corresponding to the use mode;
resetting the baseline biometrics indicating the stress level on the user according to the responses; and
generating a new AR environment of the one or more AR environment according to the use mode configuration, wherein the new AR environment is devised to induce another response closer to the range of the goal response than the responses to the AR environment.

11. The computer program product of claim 8, the selecting comprising:
validating the AR environment content for authorization to use, by checking if the AR environment content is a public domain content, a custom content provided by the user, a type of permission provided by an author of the AR environment content, and authorization applicable to respective users including the user.

12. The computer program product of claim 8, wherein the user profile includes demographic information of the user that may be utilized for psychologically meaningful classifications with respect to user response, conditions relevant to individual stress response of the user, a scale of stress levels on the user corresponding to respective biometrics measurements, and user history.

13. The computer program product of claim 8, wherein the use mode is selected from a Rehearsal mode, a Stress Relief mode, an Investigation mode, and wherein the use mode may operate either on-line or off-line.

14. The computer program product of claim 13, wherein the use mode is the Rehearsal mode and is operating on-line, the AR environment content includes a real-time data feed from one or more preselected participant reacting to a performance by the user in the AR environment.

15. A system comprising:
a memory;
one or more processor in communication with the memory; and
program instructions executable by the one or more processor via the memory to perform a method for cognitively managing a stress level on a user, comprising:
preparing a user profile corresponding to the user, the user profile including baseline biometrics for the stress level on the user and conditions affecting the stress level on the user in responding to one or more augmented reality (AR) environment, as delivered by a user AR device, and responses by the user to the one or more AR environment being monitored by one or more Internet of Things (IoT) device configured for the user;
determining a use mode for the one or more AR environment, wherein the use mode corresponds to a use mode configuration specifying how to generate the one or more AR environment for the user to attain purposes of the use mode;
selecting AR environment content for the one or more AR environment based on the user profile and the use mode, wherein the AR environment content includes audio-visual contents curated for respective stress effects to the stress level on the user;
determining a goal response for the user as being presented with the one or more AR environment, based on the user profile and the use mode;
generating an AR environment of the one or more AR environment by use of the AR environment content from the selecting according to the use mode configuration; and
sending the AR environment resulted from the generating to the user AR device for the user to experience the AR environment.

16. The system of claim 15, further comprising:
obtaining the responses by the user to the AR environment from the one or more IoT device; and
ascertaining, by use of one or more cognitive analysis tool, that the responses resulted from the obtaining are within a range of the goal response corresponding to the use mode.

17. The system of claim 15, further comprising:
obtaining the responses by the user to the AR environment from the one or more IoT device;
ascertaining, by use of one or more cognitive analysis tool, that the responses resulted from the obtaining are out of a range of the goal response corresponding to the use mode;
resetting the baseline biometrics indicating the stress level on the user according to the responses; and
generating a new AR environment of the one or more AR environment according to the use mode configuration, wherein the new AR environment is devised to induce another response closer to the range of the goal response than the responses to the AR environment.

18. The system of claim 15, the selecting comprising:
validating the AR environment content for authorization to use, by checking if the AR environment content is a public domain content, a custom content provided by the user, a type of permission provided by an author of the AR environment content, and authorization applicable to respective users including the user.

19. The system of claim 15, wherein the user profile includes demographic information of the user that may be utilized for psychologically meaningful classifications with respect to user response, conditions relevant to individual stress response of the user, a scale of stress levels on the user corresponding to respective biometrics measurements, and user history.

20. The system of claim 15, wherein the use mode is selected from a Rehearsal mode, a Stress Relief mode, an Investigation mode, and wherein the use mode may operate either on-line or off-line, and wherein, while the use mode is the Rehearsal mode and is operating on-line, the AR environment content includes a real-time data feed from one or more preselected participant reacting to a performance by the user in the AR environment.

21. A computer implemented method for cognitively managing a stress level on a user, comprising:
preparing, by one or more processor, a user profile corresponding to the user, the user profile including baseline biometrics for the stress level on the user and conditions affecting the stress level on the user in responding to one or more augmented reality (AR) environment, as delivered by a user AR device, and responses by the user to the one or more AR environment being monitored by one or more Internet of Things (IoT) device configured for the user;
determining, by the one or more processor, a use mode for the one or more AR environment, wherein the use mode corresponds to a use mode configuration specifying how to generate the one or more AR environment for the user to attain purposes of the use mode;
selecting, by the one or more processor, AR environment content for the one or more AR environment based on the user profile and the use mode, wherein the AR environment content includes audio-visual contents curated for respective stress effects to the stress level on the user;
determining, by the one or more processor, a goal response for the user as being presented with the one or more AR environment, based on the user profile and the use mode;
generating, by the one or more processor, an AR environment of the one or more AR environment by use of the AR environment content from the selecting according to the use mode configuration;
sending, by the one or more processor, the AR environment resulted from the generating to the user AR device for the user to experience the AR environment;
obtaining the responses by the user to the AR environment from the one or more IoT device; and
ascertaining, by use of one or more cognitive analysis tool, that the responses resulted from the obtaining are within a range of the goal response corresponding to the use mode.

22. The computer implemented method of claim 21, the selecting comprising:
validating the AR environment content for authorization to use, by checking if the AR environment content is a public domain content, a custom content provided by the user, a type of permission provided by an author of the AR environment content, and authorization applicable to respective users including the user, wherein the use mode is selected from a Rehearsal mode, a Stress Relief mode, an Investigation mode, wherein the use mode may operate either on-line or off-line.

23. A computer implemented method for cognitively managing a stress level on a user, comprising:
preparing, by one or more processor, a user profile corresponding to the user, the user profile including baseline biometrics for the stress level on the user and conditions affecting the stress level on the user in responding to one or more augmented reality (AR) environment, as delivered by a user AR device, and responses by the user to the one or more AR environment being monitored by one or more Internet of Things (IoT) device configured for the user;
determining, by the one or more processor, a use mode for the one or more AR environment, wherein the use mode corresponds to a use mode configuration specifying how to generate the one or more AR environment for the user to attain purposes of the use mode;
selecting, by the one or more processor, AR environment content for the one or more AR environment based on the user profile and the use mode, wherein the AR environment content includes audio-visual contents curated for respective stress effects to the stress level on the user;
determining, by the one or more processor, a goal response for the user as being presented with the one or more AR environment, based on the user profile and the use mode;
generating, by the one or more processor, an AR environment of the one or more AR environment by use of the AR environment content from the selecting according to the use mode configuration;
sending, by the one or more processor, the AR environment resulted from the generating to the user AR device for the user to experience the AR environment;
obtaining the responses by the user to the AR environment from the one or more IoT device;
ascertaining, by use of one or more cognitive analysis tool, that the responses resulted from the obtaining are out of a range of the goal response corresponding to the use mode;
resetting the baseline biometrics indicating the stress level on the user according to the responses; and
generating a new AR environment of the one or more AR environment according to the use mode configuration, wherein the new AR environment is devised to induce another response closer to the range of the goal response than the responses to the AR environment.

24. The computer implemented method of claim 23, the selecting comprising:
- validating the AR environment content for authorization to use, by checking if the AR environment content is a public domain content, a custom content provided by the user, a type of permission provided by an author of the AR environment content, and authorization applicable to respective users including the user.

25. The computer implemented method of claim 23, wherein the use mode is selected from a Rehearsal mode, a Stress Relief mode, an Investigation mode, wherein the use mode may operate either on-line or off-line.

\* \* \* \* \*